United States Patent
Schinski et al.

(10) Patent No.: US 7,282,617 B2
(45) Date of Patent: Oct. 16, 2007

(54) PROCESS OF MAKING A HIGHLY STABLE AROMATIC ALKYLATE SUITABLE FOR USE IN MAKING IMPROVED ADDITIVES AND SURFACTANTS

(75) Inventors: William L. Schinski, San Rafael, CA (US); Curt B. Campbell, Hercules, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 40 days.

(21) Appl. No.: 11/395,746

(22) Filed: Mar. 31, 2006

(65) Prior Publication Data

US 2006/0224026 A1  Oct. 5, 2006

Related U.S. Application Data

(60) Provisional application No. 60/667,467, filed on Mar. 31, 2005.

(51) Int. Cl.
*C07C 2/66* (2006.01)
*C07C 4/16* (2006.01)
*C07C 4/18* (2006.01)
*C07C 39/06* (2006.01)
*C07C 37/14* (2006.01)

(52) U.S. Cl. ...................... 585/455; 585/457; 585/486; 585/489; 568/781; 568/789; 568/794

(58) Field of Classification Search ................ 585/455, 585/457, 486, 489; 568/781, 789, 794
See application file for complete search history.

(56) References Cited

U.S. PATENT DOCUMENTS 6,096,938 A * 8/2000 Ghosh ......................... 585/486

* cited by examiner

*Primary Examiner*—Peter O'Sullivan
(74) *Attorney, Agent, or Firm*—Steven H. Roth

(57) ABSTRACT

A process for making medium and long chain alkylaromatics and alkylphenols having a high level of anti-Markovnikov addition of the alkyl group. The alkylaromatics and alkylphenols made by the process of the present invention have enhanced stability and are particularly well suited to make highly stable oil additives and enhanced oil recovery surfactants.

8 Claims, No Drawings

PROCESS OF MAKING A HIGHLY STABLE AROMATIC ALKYLATE SUITABLE FOR USE IN MAKING IMPROVED ADDITIVES AND SURFACTANTS

CROSS REFERENCE TO RELATED APPLICATIONS

This application is based on and claims priority from U.S. Provisional Application 60/667,467 filed Mar. 31, 2005 which is incorporated by reference herein in its entirety.

BACKGROUND OF THE INVENTION

Medium to long chain alkyl aromatics are used to make high volume additives and surfactants. Examples of such compounds are alkyl aromatic sulfonates used in lubricant additives. Alkyl aromatic sulfonates are also used in surfactants such as detergents. Another potential use for alkyl aromatic sulfonates is in Enhanced Oil Recovery (EOR) chemicals where EOR chemical is used to increase the productivity of an oil field. Different chain lengths and branching of the alkyl chain of the alkyl aromatic are used depending on the application. The thermal and oxidative stability of alkyl aromatic based additives and surfactants is increasingly important and desirable in specific uses. In the area of lubricant additives the lubricants are being subjected to more severe conditions and longer drain intervals and the desire is to have lubricant compositions that are stable longer. In EOR chemicals it is highly desired to have surfactants that are stable for long periods of time at very extreme temperatures and pressures. An EOR chemical may have to be active for several years. Dealkylation of significant amounts of the alkylaromatic sulfonate can lead to loss of activity of the EOR chemical. Likewise dealkylation of an alkyl aromatic lubricant additive is counterproductive to the goal of increased miles between oil changes and to maintain performance.

A particular type of alkyl aromatic used to make oil additives are alkyl phenols used to make phenates. Phenates can be used in oil additives as sulfurized metal phenates. Phenate based oil additives and methods of making them are discussed in U.S. Pat. Nos. 3,178,368, 3,367,867, and 4,927,551 all of which are herein incorporated by reference in their entirety. Processes for making specific alkyl phenol isomers are disclosed in U.S. Pat. Nos. 4,532,368, 4,538,008, and 4,447,657 all which are incorporated herein by reference.

Methods for making alkylaromatic sulfonate surfactants and desired features of the alkyl groups are discussed in U.S. Pat. Nos. 6,602,840 and 6,566,319 which are herein incorporated by reference in their entirety.

Desired characteristics of, and methods of making alkyl aromatic sulfonates suitable for use as EOR chemicals are disclosed in U.S. Pat. Nos. 6,269,881 and 6,765,106 which are incorporated herein in their entirety.

In most alkylaromatic sulfonate processes the alkylaromatic is made by the alkylation of an aromatic such as benzene, toluene, phenol or xylenes, with a long chain monoolefin such as a Normal Alpha Olefin (NAO). NAOs are available in a number of specific chain lengths. In the conventional alkylation of an aromatic with an NAO the aromatic tends to attach to the 2 position of the olefin in higher than statistical proportions to form a methyl branched linear alkyl aromatic where a methyl or higher branch is attached to the carbon that is attached to the aromatic as shown below:

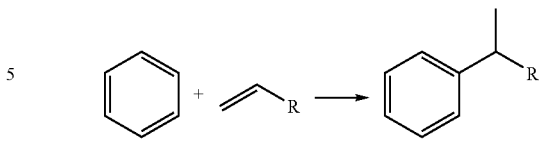

As mentioned above in some of the applications using alkyl aromatics and alkyl aromatic sulfonates high temperature conditions can be employed. Under high temperature, severe oxidative and or thermal conditions dealkylation of the alkyl group of the alkyl aromatic or alkyl aromatic sulfonate can occur. A secondary branched carbon center (secondary alkylate) can be a good leaving group under such severe conditions. A tertiary center (tertiary alkylate) provides even a better leaving group thus is even less stable. An alkyl aromatic having a primary center (primary alkylate) is more stable but as discussed above is not favored in conventional alkylation chemistry. Thus a method of making a more stable alkyl aromatic and alkyl aromatic sulfonate would be useful. The present invention provides such a method.

SUMMARY OF THE INVENTION

The present invention provides a process for making an improved intermediate that can be used to make particularly stable additives and surfactants. In particular the additives and surfactants made from the intermediates of the present invention are less prone to dealkylation under severe thermal and/or oxidative conditions than conventional additives and surfactants. In a preferred embodiment of the present invention the intermediates can be used to make EOR chemicals and/or lubricant additives. The present invention involves a method of making highly stable alkyl aromatics that have improved oxidative and/or thermal stability. The materials particularly have improved thermal and acid stability. The invention uses the surprising finding that using a particular class of catalysts alkylation of an aromatic with an olefin forms a mixture containing high levels of alkyl aromatics without the typical methyl branch on the benzyl carbon as discussed above. This reaction is referred to as "anti-Markovnikov" addition. Typically in the process of the present invention the anti-Markovnikov alkylate can be over 50%, preferably 60-80% or more of the mixture. The thus produced alkyl aromatic is much less prone to dealkylation under many severe use conditions.

In a particular embodiment of the present invention a Process for the Production of alkyl aromatics is described. The process comprises; passing a feed comprising at least one olefin species and at least one aromatic species over a catalyst having anti-Markovnikov activity, at alkylation conditions, to form an intermediate alkylate having at least 50% anti-Markovnikov addition; and, subjecting the intermediate alkylate to mild dealkylation conditions to form a product stream having an enhanced amount of anti-Markovnikov addition compared to the intermediate alkylate.

Among other factors a preferred embodiment of the present invention is based on the surprising findings that highly stable alkyl aromatics can be made by a process that uses anti-Markovnikov alkylation and selective dealkylation to make intermediates having an enhanced amount of desired product. The process of the present invention can be used to make alkylate having a high degree of primary alkylate or a high degree secondary alkylate or a desired combination thereof depending on the nature of the feedstock olefin and the amount of selective dealkylation achieved. The highly stable alkyl aromatic intermediates can be used to make improved additives, detergents, and EOR chemicals. The process can also make alkyl aromatic intermediates that are particularly tailored for the end use in the degree of branching and the placement of alkyl branching.

DETAILED DESCRIPTION OF THE INVENTION

Markovnikov's rule as stated in *Morrison and Boyd* 3$^{rd}$ Ed. Page 188 is as follows: "In the Ionic addition of an acid to the carbon-carbon double bond of an alkene, the hydrogen of the acid attaches itself to the carbon atom that already holds the greater number of hydrogens."

For the purposes of the present invention the terms anti-Markovnikov addition, anti-Markovnikov alkylation, or simply the abbreviations 'anti' addition or 'anti' alkylation is used to describe the reaction of an aromatic molecule with an olefin (alkene) where the carbon atom of the olefin that holds the greater number of hydrogens attaches to the aromatic molecule. In the case of an alpha olefin (where the double bond is between the first and second carbon atom) the terminal (first) carbon atom of the olefin attaches to the aromatic.

The terms aromatic, aromatic molecule, aromatic moiety are intended to include any molecule having an aromatic structure within the conventional chemical meaning of the term. The chemical meaning of the term aromatic is further discussed and explained in chapter 10 of in *Morrison and Boyd* 3$^{rd}$ Ed. starting on page 318 which is herein incorporated by reference in its entirety for background purposes. More specifically the term aromatic or aromatic hydrocarbon used in the present invention is a cyclic compound wherein a pi electron orbital is delocalized. This can include monocyclic and polycyclic compounds. Specifically, it is preferably an aromatic having 6 to 20 carbon atoms, and more preferably 6 to 12 carbon atoms. At least one atom of the aromatic ring has hydrogen which is covalently bonded with the atom. Such an aromatic can optionally contain a substituent. The substituent may be straight-chain, branched, or cyclic hydrocarbon. Examples of substituents include, but are not limited to, an alkyl group, a cycloalkyl group, an aryl group, an alkaryl group, an aralkyl group and the like. Examples of the alkyl group include, but are not limited to, methyl group, ethyl group, isopropyl group, n-propyl group, isobutyl group, n-butyl group, sec-butyl group, tert-butyl group and the like. Examples of the cycloalkyl group include, but are not limited to, cyclopropyl group, cyclobutyl group, cyclopentyl group, cyclohexyl group and the like. Examples of the aryl group include, but are not limited to, a phenyl group, a naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylxylyl group (mesityl group) and the like. Examples of the aralkyl group include, but are not limited to, phenylmethyl group (benzyl group), phenylethyl group (phenethyl group), triphenylmethyl group (trityl group) and the like.

The aromatic and substituent of the aromatic can further contain one or more than one non-hydrocarbon substituents having one or more atoms other than hydrogen and carbon. Examples of the non-hydrocarbon substituent include, but are not limited to, a halogen atom(s) (—F, —Cl, —Br, —I), hydroxyl group (—OH), alkoxy groups (—OR), carboxyl group (—COOH), ester groups (—COOR), aldehyde group (—CHO), acyl groups (—C(=O)R), amide group (—C(=O)NH$_2$), substituted amide groups (—C(=O)NHR), —C(=O)NR$_2$), amino group (—NH$_2$), substituted amino groups (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide groups (—CF$_3$) and the like. Preferably, the aromatic and substituent of the aromatic are those which do not poison an iridium catalyst described below and/or do not induce an undesirable secondary reaction.

Specific examples of the monocyclic aromatic include, but are not limited to, benzene, methylbenzene (toluene), 1,2-dimethylbenzene (o-xylene), 1,3-dimethylbenzene (m-xylene), 1,4-dimethylbenzene (p-xylene), 1,3,5-trimethylbenzene (mesitylene), 1,2,3-trimethylbenzene, 1,2,4-trimethylbenzene, tetramethylbenzene, pentamethylbenzene, ethylbenzene, n-propylbenzene, isopropylbenzene (cumene), 1-isopropyl-4-methylbenzene (p-cymene), n-butylbenzene, 2-butylbenzene, isobutylbenzene, tert-butylbenzene, n-pentylbenzene, cyclopentylbenzene, neopentylbenzene, cyclohexylbenzene, 1-cyclohexyl-4-methylbenzene, cyclooctylbenzene and the like.

Specific examples of the polycyclic aromatic include, but are not limited to, biphenyl, biphenylene, terphenyl, naphthalene, azulene, anthracene, phenanthrene, triphenylene, pyrene, 1-methylnaphthalene, 2-methylnaphthalene, 1-ethylnaphthalene, 2-ethylnaphthalene, 2,2'-dimethylbiphenyl, diphenylethane, 1,2-diphenylethane, 1,8-diphenyloctane and the like.

Specific examples of the aromatic containing a heteroatom include, but are not limited to, methoxybenzene (anisole), ethoxybenzene, nitrobenzene, methyl benzoate, ethyl benzoate, isobutyl benzoate, diphenyl ether, cyclohexyl phenyl ether, benzonitrile, phenyl acetate, phenyl hexanoate, tolyl acetate, phenol, benzaldehyde, acetophenone, chlorobenzene, 2-chloroxylene, bromobenzene, trichlorobenzene, 1,4-dichlorobenzene, 1,2-dibromobenzene, substituted phenols and the like.

Specific examples of more preferred aromatics are benzene, methylbenzene (toluene), ethylbenzene, xylenes, phenol, and naphthalene.

The olefin used in the present invention is a compound having at least one carbon-carbon double bond, and any straight-chain, branched and cyclic compound can be used. Specifically, it is preferably an olefin having 2 to 40 carbon atoms, preferably, 8 to 40 carbon atoms, more preferably 8 to 30 carbon atoms. Such an olefin can contain a substituent. The substituent may be straight-chain, branched, or cyclic hydrocarbon. Examples of the substituent include, but are not limited to, alkyl group, cycloalkyl group, aryl group, alkaryl group, aralkyl group and the like. Examples of the alkyl group include, but are not limited to, methyl group, ethyl group, isopropyl group, n-propyl group, isobutyl group, n-butyl group, sec-butyl group, tert-butyl group and the like. Examples of the cycloalkyl group include, but are not limited to, cyclopropyl group, cyclobutyl group, cyclopentyl group, cyclohexyl group and the like. Examples of the aryl group include, but are not limited to, phenyl group, naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4- xylyl group), 2,4,6-trimethylxylyl group (mesityl group) and the like. Examples of the aralkyl group include, but are not limited to, phenylmethyl group (benzyl group), phenylethyl group (phenethyl group), triphenylmethyl group (trityl group) and the like. Examples of the unsaturated hydrocarbon substituent include, but are not limited to, vinyl group, allyl group and the like.

The olefin and substituent of the olefin can further contain one or more than one non-hydrocarbon substituents having one or more atoms other than hydrogen and carbon. Examples of the non-hydrocarbon substituent include, but are not limited to, halogen atoms (—F, —Cl, —Br, —I), hydroxyl group (—OH), alkoxy groups (—OR), carboxyl group (—COOH), ester groups (—COOR), aldehyde group (—CHO), acyl groups (—C(=O)R), amide group (—C(=O)NH$_2$), substituted amide groups (—C(=O)NHR), —C(=O)NR$_2$), amino group (—NH$_2$), substituted amino groups (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide groups (—CF$_3$) and the like. Preferably, the olefin and substituent of the olefin are those which do not poison an iridium catalyst described below and/or do not induce an undesirable secondary reaction.

Specific examples of the straight-chain monoolefin include, but are not limited to, ethylene, propylene, 1-butene, 2-butene, straight-chain pentene (e.g. 1-pentene, 2-pentene, etc.), straight-chain hexene (e.g. 1-hexene, 2-hexene, 3-hexene, etc.), straight-chain heptene (e.g. 1-heptene, etc.), straight-chain octene (e.g. 1-octene, etc.), straight-chain nonene (e.g. 1-nonene, etc.), straight-chain decene (e.g. 1-decene, etc.), straight-chain dodecene (e.g. 1-dodecene, etc.), and straight-chain eicosene (e.g. 1-eicosene, etc.).

Specific examples of the branched monoolefin include, but are not limited to, isobutene (2-methylpropylene), 2-methyl-1-butene, 3-methyl-1-butene, 2,3,3-trimethyl-1-butene, 2-methyl-2-butene, vinylidenes and the like.

Specific examples of the cyclic monoolefin include, but are not limited to, cyclopentene, methylcyclopentene, cyclohexene, 1-methylcyclohexene, 3-methylcyclohexene, 1,2-dimethylcyclohexene, cyclooctene and the like.

Specific examples of the polyolefin include, but are not limited to 1,3-butadiene, 1,3-pentadiene, 1,5-heptadiene, divinylbenzene, vinylcyclohexene, allylcyclohexene and the like.

Specific examples of the olefin containing one or more than one heteroatoms include, but are not limited to, vinyl chloride, vinyl fluoride, vinylidene chloride, allyl bromide, chlorostyrene, trichloroethylene, acrylic acid, crotonic acid, maleic acid, methyl maleate, p-vinylbenzoic acid, vinyl acetate, allyl propionate, propenyl acetate, ethylidene diacetate, methyl acrylate, methyl methacrylate and the like.

Specific examples of more preferred olefins are alpha olefins having a carbon number of $C_4$ to $C_{40}$ and mixtures thereof. This can include cuts comprising a range of carbon number olefins, narrow cuts containing predominantly one carbon number, or discontinuous ranges of carbon numbers (e.g. $C_{12}$ to $C_{16}$ and $C_{24}$ to $C_{30}$).

A preferred source of olefins useable in the present invention is cracked wax, more preferably cracked Fischer-Tropsch wax. A patent that discloses the formation of olefins by cracking of wax is U.S. Pat. No. 6,497,812 which is herein incorporated by reference in its entirety.

Another preferred source of olefins useable in the present invention are normal alpha olefins (NAOs) which are made by the oligomerization of ethylene.

The figure below shows the two competing alkylation reactions using an alpha olefin and an aromatic. In this figure the first product (1) is a result of Markovnikov addition. (1) can be referred to as a 2° benzyl product or secondary alkylate. The second product shown (2) is the result of anti-Markovnikov or 'anti' addition. The addition is at the terminal carbon atom of the olefin and can be referred to as 1° benzyl product or primary alkylate.

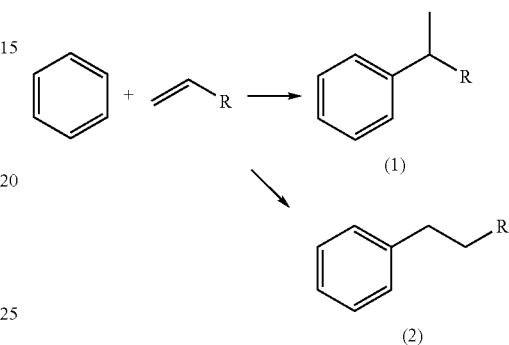

Using the most commonly employed alkylation catalysts, Markovnikov addition (1) predominates and very little if any 'anti' addition occurs. In the process of the present invention anti-Markovnikov alkylate (2) is formed and in a preferred embodiment of the present invention the 'anti' alkylate can be enhanced by selective dealkylation.

A preferred catalyst used in the alkylation step of the present invention contains iridium. The iridium complex having a beta-diketonato ligand, which is used as the preferred catalyst in the method of the present invention, is a complex having at least one iridium atom and at least one beta-diketonato ligand. This type of catalyst has been shown to have good anti-Markovnikov alkylation activity.

In a particular embodiment of the present invention the catalyst used is an Iridium containing 'Periana' catalyst. These catalysts are discussed in J. Am. Chem. Soc. 122, 7414 (2000) which is herein incorporated by reference for background purposes. Further discussion of the Iridium containing 'Periana' type catalysts and methods of making are described in U.S. Pat. No. 6,504,070 which is herein incorporated by reference in its entirety. In an embodiment of the present invention the particular class of catalysts used in the present invention can be used in conjunction with a dealkylation or selectively degrading (decoupling of the weak isomers) preferably with an acid and then either removing the fragments or recoupling in order to increase the preferred "anti-Markovnikov" content. For example if the "anti" selectivity of the coupling is 80%; a degradation/recoupling can yield a mix containing about 88% "anti" or more. Stripping of the fragments could give even higher isomer selectively. Examples could include the tertiary benzyl impurities formed from vinylidenes and tri-substituted olefins in normal alpha olefins (NAOs) or when high vinylidene polyisobutylene (PIB) is used. Alkylation of an aromatic with a vinylidene tends to form a tertiary center (3° benzyl) as shown below. A tertiary benzyl group forms a particularly good leaving group under severe (high temperature) or oxidative or acid conditions. As leaving groups 3° > 2° > 1°. Thus having a tertiary benzyl center in a lubricant additive can be very undesirable. This embodiment may be particularly useful for making precursors for the pharmaceutical or Ag-Chem industries where having a specific isomer can be particularly important.

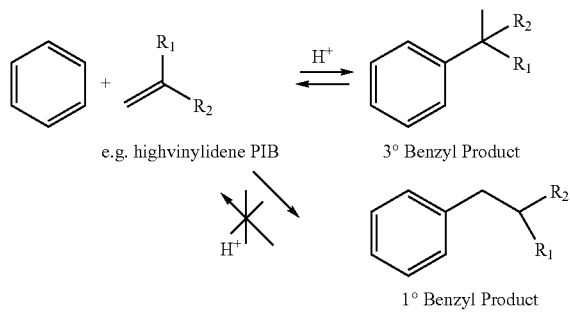

e.g. highvinylidene PIB    3° Benzyl Product

1° Benzyl Product

In the reaction shown above the 3° benzyl product may also be referred to as tertiary alkylate and the 1° benzyl product is also referred to as primary alkylate. A 2° benzyl product is also referred to as secondary alkylate. In the reaction of an NAO containing vinylidenes and or tri-substituted olefins with an aromatic compound or compounds, a mixture comprising primary alkylate, secondary alkylate, and tertiary alkylate can be formed. In an embodiment of the present invention the amounts of tertiary alkylate if present and secondary alkylate can be reduced by a selective dealkylation step. Such a dealkylation results in an enhanced stability alkylate product. Dealkylation of alkyl aromatics is described in detail in U.S. Pat. Nos. 4,045,506, 5,811,623 and 4,499,321 all of which are herein incorporated by reference in their entirety. Dealkylation in the present invention can be performed in the presence of a catalyst or can be noncatalytic. A preferred catalyst comprises silica. Another preferred catalyst comprises silica and alumina.

As mentioned above in the process of the present invention dealkylation can be either noncatalytic or catalytic. Silica-based catalysts useful in the dealkylation reaction are well known in the art. In general, silica-based catalysts which contain an acidic oxide promoter, for example alumina or magnesia, are preferred. Silica-alumina catalysts are especially preferred. Accordingly, suitable silica-based dealkylation catalysts usually contain less than about 35%, preferably from about 5% to about 25% by weight of an acidic oxide promoter. These compositions are in a state of very slight hydration, and may contain small amounts of other material such as novolatile oxides.

Other suitable silica-based catalysts include aluminum silicates produced either from natural clays by activation or by purely synthetic methods. The activation of natural clays, mostly of the montmorillonite type, is carried out by treatment with dilute acids, which remove excess alumina and oxides of calcium, iron, etc., and thus enrich the silica content. Not only clays but also other aluminum silicates, such as molecular sieve zeolites, feldspar and the like when activated are suitable silica-based dealkylation catalysts.

The production of synthetic silica-based catalysts can be performed, for instance, by impregnating silica with aluminum salts; by direct combination of precipitated (or gelated) hydrated alumina and silica in appropriate proportions; or by joint precipitation of alumina and silica from an aqueous solution of aluminum and silicon salts. Synthetic silica-based catalysts may be produced by combination or hydrated silica with other hydrate bases as, for instance, magnesia or zirconia. The activated or calcined natural or synthetic catalysts must be relatively free of impurities such as alkaline salts and ferric oxide. The presence of such impurities causes sintering of the catalyst surface on regeneration and a consequent drop in catalytic activity.

During the above described dealkylation reaction rapid separation of olefinic product and process control of conversion and temperature are critical. It has been found that by controlling these variables the silica-based dealkylation catalysts may be employed to catalyze the desired dealkylation without undesirable side reactions, such as skeletal isomerization, polymerization and disproportionation. More particularly, it has been found that at moderately high conversions of from about 70% to about 80%, based on product weight, and temperatures below about 300 degrees C. and with separation of the olefin as it is formed, the regenerated olefin is essentially consistent in skeletal arrangement and molecular weight (MW) with the initial feedstock olefin; whereas, at higher conversions, higher temperatures, or excess contact time with the catalyst, the product will contain significant amounts of skeletally isomerized olefin and increasing amounts of polymeric material. Obviously control over isomerization is particularly important where linear olefins are the desired product. Depending on the nature of the alkylate present, dealkylation generally starts at about 240 degree. C. To maintain a steady dealkylation rate, it can be preferable to gradually increase temperature to about 300 degree C. or more.

The dealkyation conditions must be carefully selected and controlled in order to maintain the desired selectivity. For instance if primary alkylate is the desired end product the dealkylation conditions must be selected to minimize dealkylation of primary alkylate but maximize dealkylation of secondary alkylate and tertiary alkylate (if present). If secondary alkylate or a mixture of secondary and primary alkylate is the desired end product the dealkylation conditions must be adjusted to maximize the dealkylation of the tertiary alkylate but avoid substantial dealkylation of the desired end product.

The dealkylation step can also be thermal (no catalyst present). Generally this requires higher temperatures than catalytic dealkylation but avoids the problems of catalyst fouling and catalyst deactivation. It may however be harder to control to maintain the desired selectivity.

On-line real time process control systems can be used to help maintain the selectivity of the dealkylation step in both catalytic and non-catalytic dealkyation. The amount of dealkylation of the different species can be monitored periodically or continuously. One such device that can be used is a gas chromatograph (GC). The GC or other device can provide feedback on the selectivity of the dealkylation reaction. The dealkylation conditions can be adjusted in response to the feedback.

In another embodiment of the present invention olefin formed in the dealkylation step is recovered. It should be noted that the olefin recovered from the dealkylation step will generally be internal.

In yet another optional embodiment of the present invention olefin formed in the dealkylation step is recovered and a portion of the recovered olefin is recycled to the alkylation step. This may be desirable depending on the desired structure of the end product. As mentioned above the olefin formed by the dealkylation reaction will generally contain internal olefins which may not be a desired feed if a primary alkylate is the desired product. However if a secondary alkylate is desired recycling may be viable.

In another embodiment of the present invention aromatics can be recovered from the dealkylation step and optionally can be recycled to make up part of the feed to the alkylation reaction.

In another embodiment of the present invention it has been surprisingly found that in the process of the present invention that the catalyst used in the present invention is not inhibited by low levels of water for the alkylation of an aromatic such as benzene with olefins. Water is often present in small amounts as an impurity in the presence of phenols. Hence in a particular embodiment of the present invention alkylation of phenols to make phenate detergent additives can be achieved:

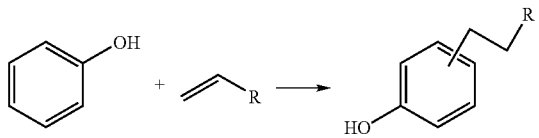

What is claimed is:

1. A process for the production of alkyl aromatics, comprising:
    passing a feed comprising at least one olefin species and at least one aromatic species over a catalyst having anti-Markovnikov activity, at alkylation conditions, to form an intermediate alkylate having at least 50% anti-Markovnikov addition;
    subjecting the intermediate alkylate to mild dealkylation conditions, optionally in the presence of a dehydrogenation catalyst, to form a selectively dealkylated effluent stream; and
    recovering from the dealkylated effluent stream, a product stream having an enhanced amount of anti-Markovnikov alkylate.

2. A process for making alkylphenols, comprising:
    passing a feed comprising phenol and an olefin over a catalyst having anti-Markovnikov activity, at alkylation conditions, to form an alkylphenol having at least 50% anti-Markovnikov composition.

3. A process for the production of alkyl aromatics, comprising:
    passing a feed comprising alpha olefins, vinylidenes, and aromatic compounds over a catalyst having anti-Markovnikov activity, at alkylation conditions, to form an intermediate alkylate having at least 50% anti-Markovnikov addition and comprising primary alkylate, secondary alkylate and tertiary alkylate; and
    subjecting the intermediate alkylate to mild dealkylation conditions, optionally in the presence of a dehydrogenation catalyst, to form a product stream having an enhanced amount of anti-Markovnikov alkylate.

4. The process of claim 1 wherein a stream comprising olefins is recovered from the selectively dealkylated effluent stream.

5. The process of claim 4 wherein at least a portion of the stream comprising olefins is recycled to become a portion of the feed.

6. The process of claim 1 wherein the mild dehydrogenation conditions comprise a temperature below about 300 degrees C.

7. The process of claim 1 wherein the mild dehydrogenation conditions comprise a temperature below about 280 degrees C.

8. The process of claim 1 wherein the dehydrogenation catalyst comprises silica.

* * * * *